United States Patent [19]
Remy

[11] 3,974,285
[45] Aug. 10, 1976

[54] 10,11-FURO-DERIVATIVES OF CYPROHEPTADINE

[75] Inventor: David C. Remy, North Wales, Pa.

[73] Assignee: Merck & Co., Inc., Rahway, N.J.

[22] Filed: Jan. 30, 1975

[21] Appl. No.: 545,646

Related U.S. Application Data

[62] Division of Ser. No. 459,493, April 10, 1974, Pat. No. 3,894,032.

[52] U.S. Cl. .......................... 424/267; 260/293.58; 260/293.62
[51] Int. Cl.² .................................... C07D 405/10
[58] Field of Search ............... 260/293.58; 424/267

[56] References Cited
UNITED STATES PATENTS

| | | | |
|---|---|---|---|
| 3,014,911 | 12/1961 | Engelhardt | 260/296.62 |
| 3,470,188 | 9/1969 | Kaiser et al. | 260/293.58 |
| 3,838,123 | 9/1974 | Viterbo et al. | 260/293.58 |

OTHER PUBLICATIONS
Tochtermann et al. Chem. Abst. 1968, vol. 69, No. 96429v.

*Primary Examiner*—Natalie Trousof
*Attorney, Agent, or Firm*—Harry E. Westlake, Jr.; James A. Arno; William H. Nicholson

[57] ABSTRACT

10,11-Furo and 10,11-bis-(hydroxyalkyl) derivatives of cyproheptadine are disclosed having anticholinergic activity but with diminished or eliminated antiserotonin and antihistamine activity. Also disclosed are processes for the preparation of such compounds; pharmaceutical compositions comprising such compounds, and methods of treatment comprising administering such compounds and compositions.

12 Claims, No Drawings

10,11-FURO-DERIVATIVES OF CYPROHEPTADINE

This is a division of application Ser. No. 459,493, filed Apr. 10, 1974, now U.S. Pat. No. 3,894,032.

BACKGROUND OF THE INVENTION

This invention relates to certain 10,11-furo; and 10,11-bis-(hydroxyalkyl)-cyproheptadine derivatives (structures I – II, and III, respectively, below) having anticholinergic, but little to no antiserotonin or antihistamine activity. This invention also relates to processes for the preparation of such derivative compounds, pharmaceutical compositions comprising such compounds; and methods of treatment comprising adminstering such compounds and compositions.

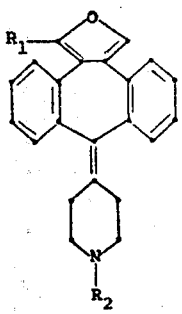

I

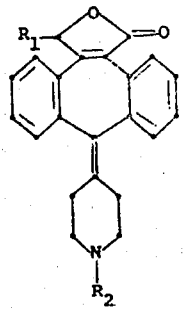

II

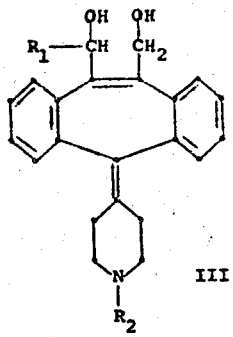

III

With respect to the above structures which represent the compounds of the present invention, $R_2$ is lower alkyl having from 1 to about 5 carbon atoms; and $R_1$ is hydrogen, or lower alkyl having from 1 to about 5 carbon atoms.

The parent compound, cyproheptadine, is a known pharmaceutical having potent antihistamine, antiserotonin and anticholinergic activity. Unexpectedly, however, the compounds of this invention are exclusively anticholinergics with little or no antihistamine and antiserotonin activity.

Thus, it is an object of the present invention to prepare cyproheptadine derivatives which specifically act as anticholinergics and are free of ancillary pharmacological effects such as those associated with the parent compound, namely: antihistamine and antiserotonin activity.

It is a further object of the present invention to provide processes for the preparation of such cyproheptadine derivative compounds; to provide pharmaceutical compositions comprising such compounds; and to provide methods of treatment comprising administering such compounds and compositions, wherein anticholinergic activity is desired and wherein antihistamine/antiserotonin effects are not indicated.

DETAILED DESCRIPTION OF THE INVENTION

The preparation of the compounds of this invention (structures I, II, and III, above-depicted) is best described from inspection of the following reaction scheme:

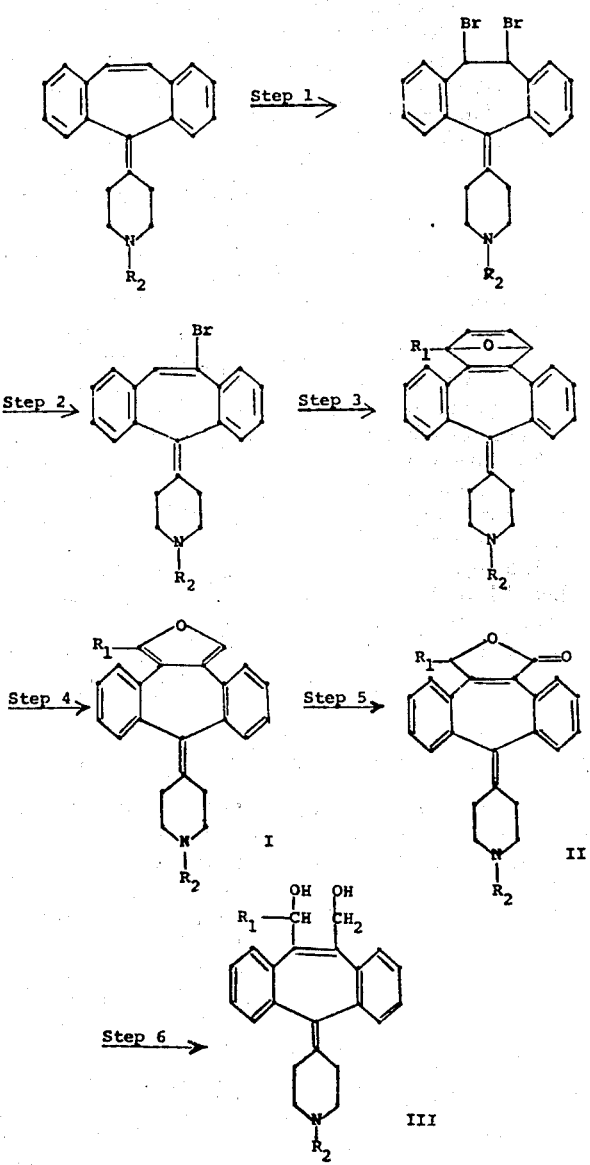

In words relative to the above reaction scheme, the starting material is cyproheptadine ($R_2$ is methyl) or higher N-alkyl homologues thereof.

Step 1 involves addition of halogen, such as bromine and the like, to the 10,11-double bond. This reaction is preferably conducted in solution. There is no criticality as to the identity of the solvent or reaction temperature. Suitable solvents include glacial acetic acid, propionic acid and the like; typically the reaction is conducted at room temperature.

Step 2 involves dehydrohalogenation of the product of Step 1 in the presence of any strong base such as alkali metal oxides, hydroxides, alkali metal alkoxides and the like. Suitable solvents may be selected from lower alkanols, such as methanol, ethanol, t-butyl alcohol and the like. Typically the reaction is conducted at from about 0° to about 50°C.

Step 3 involves the reaction of the product of Step 2 with furan or a 2-lower alkyl furan derivative in the presence of a strong base such as an alkali metal alkoxide, for example potassium-t-butoxide. Typically, the furan serves as the solvent; however other solvents such as ether, dioxane, tetrahydrofuran, and the like, may be used in admixture. The reaction is conducted at from about 0°C. to the reflux temperature.

The adduct resulting from Step 3 is then subjected to a reverse (or retro) Diels-Adler type reaction (Step 4) to provide the 10,11-furocyproheptadine derivatives of this invention (I, above). Suitable reagents for this reaction include tetraphenylcyclopentadienone, and the like, preferably in stoichiometric amount. Suitable solvents may be selected from any aprotic solvent including hydrocarbons such as xylene, and halogenated hydrocarbons, and the like. Typically the reaction is conducted at from about 100° to about 180°C.

The oxo derivative (II) of the 10,11-furocyproheptadine compounds of this invention is preferably obtained from the corresponding furo derivative (I) by treating the latter with a halogen such as bromine in the presence of a lower alkanol such as methanol and the like followed by treatment with base. Following digestion of the resulting intermediate product in a mineral acid such as HCl and the like, the desired oxo derivative of this invention is obtained (Step 5).

The 10,11-bis-(hydroxyalkyl)cyproheptadine derivative (III) of the present invention is preferably obtained from the corresponding 10,11-furanone (II) by reduction of the latter with a reducing agent such as an alkali metal aluminum hydride such as lithium aluminum hydride, and the like. Typically the reduction is conducted in a solvent such as tetrahydrofuran, dioxane, ether or the like, at a temperature of from about 25° to about 100°C.

As previously mentioned, the compounds of the present invention are anticholinergics, and are either entirely free or substantially free of the antihistamine and antiserotonin activities which characterize their parent compound, cyproheptadine. The compounds may be admnistered in capsule, tablet, fluid suspension or solution form in the amount of from 0.5 to 1000 milligrams per dose taken 2 to 4 times a day. The compounds may most easily be administered as acid addition salts and any convenient, nontoxic, pharmaceutically acceptable organic or inorganic acid may be used for this purpose. These salts, in that they are nontoxic and pharmaceutically acceptable, are considered the equivalent of the above described compounds of the present invention.

The following examples specifically illustrate, but do not limit, the product, process, and compositional aspects of the present invention.

EXAMPLE 1

A.

1-Methyl-4-(10,11-dibromo-10,11-dihydro-5H-dibenzo[a,d]-5-ylidene)piperidine hydrobromide The hydrobromide salt of cyproheptadine (18.40 g., 0.05 mole) is dissolved with warming in 750 ml. of glacial acetic acid in a 1.0 L. one neck round bottom flask equipped with a dropping funnel with equalizing side arm and magnetic stirring bar. The solution of cyproheptadine is cooled to 25°C. and 8.0 g., 2.6 ml. (0.05 mole) of bromine dissolved in 75 ml. of glacial acetic acid is added dropwise. After the addition is complete, the mixture is stirred overnight. The product is collected on a Buchner funnel and washed with a small amount of cold glacial acetic acid and then with dry ether. This product is dried 4 hours in a vacuum oven at 70° to give 20 g. (76% yield) of 1-methyl-4-(10,11-dibromo-10,11,dihydro-5H-dibenzo[a,d]-5-ylidene)piperidine hydrobromide.

B.

1-Methyl-4-(10-bromo-5H-dibenzo[a,d]cyclohepten-5-ylidene)piperidine

In a dry 1.0 l. round bottom flask containing a magnetic stirring bar is placed 600 ml. of a 0.40 molar (0.24 mole) solution of potassium t-butoxide in t-butanol. To this is added quickly 42.1 g. (0.079 mole) of the product of part A as the dry crystals. A drying tube is quickly fitted to the flask and the reaction is stirred vigorously for 6 hours at room temperature. Thereafter, the reaction mixture is poured into a 6.0 L flask filled with water and extracted three times with 500 ml. portions of benzene. The combined benzene extracts are dried over magnesium sulfate, filtered, and the benzene evaporated to dryness. There remains 27.9 g. of crude crystalline product (82%), which is dissolved in 750 ml. of boiling hexane, filtered hot, the volume reduced to 200 ml. by boiling off hexane, seeded and allowed to crystallize. The crystals are collected and dried in a vacuum oven at 60° overnight to give 23.7 g. of 1-methyl-4-(10-bromo-5H-dibenzo[a,d]cyclohepten-5-ylidene)-piperidine (m.p. 127°–129°C.).

EXAMPLE 2

1-Methyl-4-(1,4-dihydro-1,4-epoxy-9H-tribenzo[a,c,e]cycloheptene-9-ylidene)piperidine To a solution of 30.0 g. (0.0816 mole) of 1-methyl-4-(10-bromo-5H-dibenzo[a,d]cyclohepten-5-ylidene) piperidine in 600 ml. of furan is added dropwise 650 ml. of a 0.94 M solution of potassium t-butoxide in t-butanol. The mixture is stirred and refluxed gently under a nitrogen atmosphere. After 3 days, an additional 200 ml. of furan and 217 ml. of a 0.94 M solution of potassium t-butoxide in t-butanol is added, and the stirring and refluxing is continued for another 3 days. The reaction mixture is cooled and the bulk of the furan and t-butanol is removed on a rotary evaporator at 50°C. The residue, after dilution with 1 liter of water, is extracted with four 200 ml. portions of ether. The combined ether extracts are washed with water, dried over magnesium sulfate, filtered, and the ether removed on a rotary evaporator. The residue, dissolved in a minimum amount of warm absolute ethanol, is treated with an ethanolic solution of hydrogen chloride until the solution is acid. On cooling, 14.4 g. of product crystallizes. The material is recrystallized from absolute ethanol to give pure 1-methyl-4-(1,4-dihydro-1,4-epoxy-9H-tribenzo[a,c,e]cyclohepten-9-ylidene) piperidine as the hydrochloride hemiethanol solvate salt, m.p. 220°–222°.

Analysis: Calculated for $C_{25}H_{23}NO \cdot HCl \cdot 0.5\ C_2H_5OH$: C, 75.69; H, 6.57; N, 3,40; Cl, 8.61. Found: C, 75.49; H, 6.91; N, 3.31; Cl, 8.44.

EXAMPLE 3

1-Methyl-4-(8H-dibenzo[a,e]furo[3,4-c]cycloheptan-8-ylidene)piperidine

To a solution of 3.20 g. (0.0093 mole) of 1-methyl-4-(1,4-dihydro-1,4-epoxy-9H-tribenzo[a,c,e]cyclohepten-9-ylidene)-piperidine in 105 ml. of xylene (b.p. 139°–140°) is added 3.60 g. (0.00936 mole) of tetraphenylcyclopentadienone ("tetracyclone"). The solution is stirred and refluxed for 22 hours. To the cooled solution is added 100 ml. of 3N hydrochloric acid. The crystalline solid that forms is removed by filtration and is washed thoroughly with benzene and ether. The white crystalline solid is dissolved in warm water and is treated with a solution of sodium carbonate. The resulting precipitate is extracted into benzene, washed with water, dried over magnesium sulfate, filtered, and the benzene is removed on a rotary evaporator. The crystalline residue, weighing 2.62 gm., is recrystallized from absolute methanol to give 1-methyl-4-(8H-dibenzo[a,e]furo[3,4-c]cyclohepten-8-ylidene)-piperidine, m.p. 147°–148°.

Analysis: Calculated for $C_{23}H_{21}NO$: C, 84.37; H, 6.46; N, 4.28. Found: C, 84.55; H, 6.53; N, 4.23.

EXAMPLE 4

1-Methyl-4-(1-methyl-1,4-dihydro-1,4-epoxy-9H-tribenzo[a,c,e]cyclohepten-9-ylidene)piperidine To a solution of 10.0 g. (0.0273 mole) of 1-methyl-4-(10-bromo-5H-dibenzo[a,d]cyclohepten-5-ylidene)-piperidine in 50 ml. of dry ether is added 25 ml. of 2-methylfuran and 3.4 g. of potassium t-butoxide. The mixture is stirred and refluxed for 10 days. After the addition of water (1.0 l.), the mixture is extracted with an ether-benzene mixture (4:1). This organic phase is removed, washed with water, dried over magnesium sulfate, filtered, and the solvent is removed on a rotary evaporator. The residue that remains crystallizes readily to give 4.0 g. of product. The material is recrystallized from acetonitrile to give pure 1-methyl-4-(1-methyl-1,4-dihydro-1,4-epoxy-9H-tribenzo[a,c,e]cyclohepten-9-ylidene)piperidine, m.p. 175°–177°.

Analysis: Calculated for $C_{26}H_{25}NO$: C, 84.98; H, 6.86; N, 3.81. Found: C, 84.83; H, 6.88; N, 3.92.

EXAMPLE 5

1-Methyl-4-(1-methyl-8H-dibenzo[a,e]furo[3,4-c]cycloheptene-8-ylidine)piperidine A solution of 2.00 g. (0.00545 mole) of 1-methyl-4-(1-methyl-1,4-dihydro-1,4-epoxy-9H-tribenzo[a,c,e]-cyclohepten-9-ylidene)piperidine and 2.16 g. (0.0056 mole) of tetraphenylcyclopentadienone in 60 ml. of xylene (b.p. 139°–140°) is stirred and refluxed for 20 hours. After cooling, 30 ml. of 6N hydrochloric acid is added. The precipitate that forms is removed by filtration and the solid precipitate is washed with ether and benzene. The solid is collected and made basic with 40% sodium hydroxide solution. The mixture is extracted with ether, and the ether extract is washed with water and dried over magnesium sulfate. After filtration, the ether is removed to give a crystalline residue which is recrystallized from methanol to give 1-methyl-4-(1-methyl-8H-dibenzo[a,e]furo[3,4-c]cyclohepten-8-ylidene)piperidine, m.p. 80°–86°.

Analysis: Calculated for $C_{24}H_{23}NO$: C, 84.42; H, 6.79; N, 4.10. Found: C, 84.33; H, 6.88; N, 3.81.

EXAMPLE 6

1-Methyl-4-(1,3-dihydro-1-oxo-8H[3,4:6,7]cyclohepten[1,2,c]furan-8-ylidene)piperidine A solution of 3.80 g. (0.0106 mole) of 1-methyl-4-(8H-dibenzo[a,e]furo[3,4-c]cyclohepten-8-ylidene)-piperidine in a mixture of 35 ml. of methanol and 45 ml. of ether is cooled to below −40°C. in a dry ice-acetone bath. The solution is stirred, and a cold (0°C) solution of 3.80 g. of bromide in 35 ml. of methanol is added slowly over 10 minutes. After stirring for 30 minutes, ammonia is bubbled into the solution until it is just basic to pH paper. The solution is then stored overnight in a freezer (−12°C). The light yellow solution is concentrated on a rotary evaporator. The residue is dissolved in chloroform and washed with water. The chloroform is removed on a rotary evaporator, and the residue is heated on a steam bath with 100 ml. of 1N hydrochloric acid for 30 minutes. The solution is cooled and sodium carbonate (solid) is added until the solution is basic. The resulting precipitate is dissolved in chloroform, and the chloroform extract is washed with water, dried over magnesium sulfate, filtered, and the chloroform removed on a rotary evaporator. The hydrogen oxalate salt is prepared by treating the residue with an equimolar amount of oxalic acid. The resulting salt is recrystallized from methanol to give 1-methyl-4-(1,3-dihydro-1-oxo-8H-dibenzo[3,4:6,7]cyclohepten[1,2-c]furan-8-ylidene)piperidine hydrogen oxalate as the methanol solvate, m.p. 155°–158°.

Analysis: Calculated for $C_{23}H_{21}.(CO_2H)_2.CH_3OH$: C, 67.09; H, 5.85; N, 3.01. Found: C, 67.08; H, 5.34; N, 2.91.

EXAMPLE 7

1-Methyl-4-(10,11-bis-(hydroxymethyl)-5H-dibenzo[a,d]cyclohepten-5-ylidene)piperidine To a slurry of 3.61 g. of lithium aluminum hydride in 25 ml. of ether is added dropwise a solution of 2.74 g. (0.008 mole) of 1-methyl-4-(1,3-dihydro-1-oxo-8H-dibenzo[3,4:6,7]cyclohepten 1,2-c]furan-8-ylidene)-piperidine in 25 ml. of dry tetrahydrofuran. The mixture is stirred 3 days at room temperature and is finally refluxed for 4 hours. Water (4 ml.) is added, followed by the addition of 12 ml. of 5N sodium hydroxide and then another 4 ml. of water. The supernatant liquid is decanted, and the residue is extracted with four-100 ml. portions of hot tetrahydrofuran and two-100 ml. portions of boiling benzene. The original supernatant liquid and all of the extracts are combined and the solvents are removed on a rotary evaporator. The residue is recrystallized from benzene to give 1-methyl-4-(10,11-bis(hydroxymethyl)-5H-dibenzo[a,d]cyclohepten-5-ylidene)piperidine m.p. 204°–205°C.

Analysis: Calculated for $C_{23}H_{25}NO_2$: C, 79.51; H, 7.25; N, 4.03. Found: C, 79.79; H, 7.70; N, 3.93.

EXAMPLE 8

1-Methyl-4-(3-methyl-1,3-dihydro-1-oxo-8H[3,4:6,7]cycloheptene[1,2-c]furan-8-ylidene)-piperidine The procedure of Example 6 is followed, using an equivalent quantity of the product of Example 5 in place of the starting material of Example 6, to give 1-methyl-4-(3-methyl-1,3-dihydro-1-oxo-8H[3,4:6,7]cycloheptene[1,2-c]furan-8-ylidene)-piperidine.

EXAMPLE 9

1-Methyl-4-(10-hydroxymethyl-11-α-hydroxyethyl-5H-dibenzo[a,d]cyclohepten-5ylidene)piperidine The procedure of Example 7 is followed, using the product of Example 8 in place of the starting material of Example 7, to give 1-methyl-4-(10-hydroxymethyl-11-α-hydroxyethyl-5H-dibenzo-[a,d]cyclohepten-5-ylidene)-piperidine.

EXAMPLE 10

Following the procedure exactly as described in Example 4 except that there is substituted for the 2-methylfuran an equivalent quantity of 2-ethylfuran and 2-butylfuran, respectively, there is obtained the respective ethyl and butyl substituted compounds corresponding to the methyl substituted compound of Example 4.

When either the ethyl and butyl compounds, respectively, are used in the procedure of Example 8, the corresponding 1-methyl-4-(3-ethyl-and 3-butyl-cycloheptenfuranylidene)piperidines are obtained, respectively. When these compounds are used in the procedure of Example 9, in place of the product of Example 8, the corresponding 11-α-hydroxypropyl and 11-α-hydroxypentyl compounds are obtained, respectively.

EXAMPLE 11

When the N-ethyl, N-propyl and N-amyl analogues of cyproheptadine are used in the procedure of Example 1A in place of cyproheptadine, and the products are then used in the procedures of Examples 1B, 2, 3, 4, 5, 6, 7, 8, 9 and 10, in place of the N-methyl compounds used in these respective examples the corresponding 1-ethyl, 1-propyl and 1-amyl piperidine derivatives are obtained.

EXAMPLE 12

1-Methyl-4-(1,3-dihydro-1-oxo-8H[3,4:6,7]cyclohepten[1,2,c]furan-8-ylidene)piperidine hydrochloride To a saturated ethanolic solution of 1-methyl-4(1,3-dihydro-1-oxo-8H[3,4:6,7]cyclohepten[1,2,c]furan-8-ylidene)piperidine is added, dropwise, a 1.0 M solution of HCl in ethanol. The resulting salt precipitate is filtered and dried to provide 1-methyl-4-(1,3-dihydro-1-oxo-8H[3,4:6,7]cyclohepten]1,2,c]furan-8-ylideneZ)-piperidine hydrochloride.

A suitable unit dosage form of the products of this invention can be administered by mixing 50 milligrams of a 10,11-furo; 10,11-furanone; or 10,11-bis(hydroxyalkyl)-cyproheptadine derivative of this invention or a suitable acid addition salt, thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods and, if desired, can be made up as elixirs or as injectable solutions by methods well known to pharmacists.

EXAMPLE 13

Dry-filled capsules containing 50 mg. of active ingredient per capsule.

|  | Per capsule, mg. |
| --- | --- |
| 1-Methyl-4-(1,3-dihydro-1-oxo-8H[3,4:6,7]cyclohepten[1,2,c]-furan-8-ylidene)piperidine hydrochloride | 50 |
| Lactose | 149 |
| Magnesium stearate | 1 |
| Capsule (size No. 1) | 200 |

Similar dry-filled capsules can be prepared by replacing the active ingredient of the above example by any of the other novel compounds of this invention.

What is claimed is:

1. A compound of the formula:

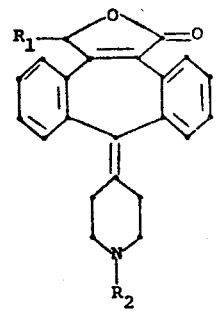

wherein $R_1$ is hydrogen or lower alkyl having from one to five carbon atoms and $R_2$ is lower alkyl having from one to five carbon atoms, and the nontoxic pharmaceutically acceptable acid addition salts thereof.

2. A compound of claim 1 wherein $R_2$ is methyl.
3. The compound of claim 2 wherein $R_1$ is hydrogen.
4. The compound of claim 2 wherein $R_1$ is methyl.
5. A pharmaceutical anticholinergic composition comprising a therapeutically effective amount of a compound having the structure:

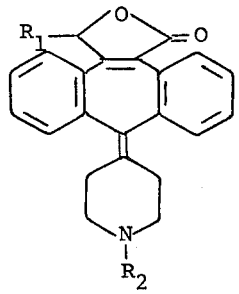

wherein $R_2$ is lower alkyl having from one to five carbon atoms, $R_1$ is hydrogen or lower alkyl having from one to five carbon atoms or a nontoxic pharmaceutically acceptable acid addition salt thereof and a pharmaceutically acceptable carrier therefor.

6. The composition of claim 5 wherein $R_2$ is methyl.
7. The composition of claim 6 wherein $R_1$ is hydrogen.
8. The composition of claim 6 wherein $R_1$ is methyl.
9. A method of treatment of a hypercholinergic condition comprising administering to a patient in need of such treatment a therapeutically effective amount of a compound having the structure:

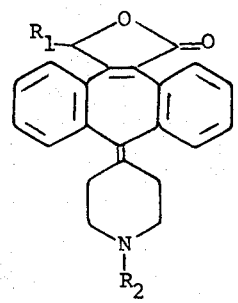

or a nontoxic pharmaceutically acceptable acid addition salt thereof, wherein $R_2$ is lower alkyl having from one to five carbon atoms and $R_1$ is hydrogen or lower alkyl having from one to five carbon atoms.

10. The method of claim 9 wherein $R_2$ is methyl.
11. The method of claim 10 wherein $R_1$ is hydrogen.
12. The method of claim 10 wherein $R_1$ is methyl.

* * * * *